(12) United States Patent
Koertge et al.

(10) Patent No.: US 7,715,907 B2
(45) Date of Patent: May 11, 2010

(54) METHOD AND SYSTEM FOR ATRIAL FIBRILLATION ANALYSIS, CHARACTERIZATION, AND MAPPING

(75) Inventors: Detlef W. Koertge, Carpentersville, IL (US); Hongxuan Zhang, Schaumburg, IL (US); Harold Wade, Noblesville, IN (US); Myrtis Randolph, Schaumburg, IL (US); Lori Palmquist, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 394 days.

(21) Appl. No.: 11/832,153

(22) Filed: Aug. 1, 2007

(65) Prior Publication Data

US 2008/0214945 A1 Sep. 4, 2008

Related U.S. Application Data

(60) Provisional application No. 60/892,676, filed on Mar. 2, 2007.

(51) Int. Cl.
*A61B 5/0402* (2006.01)
(52) U.S. Cl. .................. 600/515; 600/508; 600/509; 600/510; 600/511; 600/512; 600/554; 600/424; 703/11; 606/41
(58) Field of Classification Search ......... 600/508–512, 600/544, 424, 407, 437, 433, 9, 523; 703/11; 128/695
See application file for complete search history.

(56) References Cited

U.S. PATENT DOCUMENTS 5,479,572 A 12/1995 Marcantonio
5,542,430 A 8/1996 Farrugia et al.
6,064,906 A 5/2000 Langberg et al.
6,066,094 A * 5/2000 Ben-Haim .................. 600/437
6,106,466 A * 8/2000 Sheehan et al. ............. 600/443
6,178,347 B1 1/2001 Olsson
6,650,927 B1 * 11/2003 Keidar ....................... 600/424
6,738,664 B1 5/2004 McDaniel
7,092,751 B2 8/2006 Erkkila
7,117,029 B2 10/2006 Stridh et al.
7,123,954 B2 10/2006 Narayan et al.
7,505,810 B2 * 3/2009 Harlev et al. ................ 600/509

(Continued)

OTHER PUBLICATIONS

Dorri. F. et al., "Construction of a Finite Element Model of the Human Vertricles Taking into Account the Fiber Orientation Pattern", 2003 Summer Bioeng. Conf., Jun. 25-29.

(Continued)

*Primary Examiner*—Carl H Layno
*Assistant Examiner*—Paul J Stice
(74) *Attorney, Agent, or Firm*—Alexander J Burke

(57) ABSTRACT

A method and system for atrial fibrillation analysis, characterization, and mapping is disclosed. A finite element model (FEM) representing a physical structure of a heart is generated. Electrogram data can be sensed at various locations in the heart using an electrophysiology catheter, and the electrogram data is mapped to the elements of the FEM. Function parameters, which measure some characteristics of AF arrhythmia, are then simultaneously calculated for all of the elements of the FEM based on the electrogram data mapped to the elements of the FEM. An artificial neural network (ANN) can be used to calculate the function parameters.

29 Claims, 4 Drawing Sheets

U.S. PATENT DOCUMENTS

| | | | |
|---|---|---|---|
| 2002/0045810 A1* | 4/2002 | Ben-Haim | 600/374 |
| 2003/0018277 A1* | 1/2003 | He | 600/544 |
| 2008/0208068 A1* | 8/2008 | Robertson et al. | 600/508 |

OTHER PUBLICATIONS

Hashim, S. et al., Finite Element Method in Cardiac Surgery, Interactive Cardiovascular and Thoracic Surgery, vol. 5, 2006, pp. 5-8.

* cited by examiner

AF STRUCTURE IN HEART

FEM MAPPING AF

METHOD AND SYSTEM FOR ATRIAL FIBRILLATION ANALYSIS, CHARACTERIZATION, AND MAPPING

This application claims the benefit of U.S. Provisional Application No. 60/892,676, filed Mar. 2, 2007, the disclosure of which is herein incorporated by reference.

FIELD

Embodiments of the present invention relate to analyzing heart activity, and more particularly to a method and system for atrial fibrillation analysis, characterization, and mapping.

BACKGROUND

Atrial Fibrillation (AF) is a commonly occurring cardiac arrhythmia. In a normal heart rhythm, the impulse generated by the sinoatrial node spreads through the heart and causes contraction of the heart muscle and pumping of blood. In AF, the regular electrical impulses of the sinoatrial node are replaced by disorganized, rapid electrical impulses which result in irregular heartbeats. AF may result in symptoms of palpitations, fainting, chest pain, or heart failure, and is a leading cause of thromboembolism and stroke.

Although AF is a commonly occurring cardiac arrhythmia, the treatment of AF is difficult because there is no precise qualitative and quantitative methodology for analyzing AF in a patient. Typically, catheter ablation is used to terminate an AF arrhythmia. In catheter ablation procedures, doctors attempt to identify locations of abnormal electrical activity in the heart. The tip of a catheter is then used to apply energy (either radiofrequency to heat or liquid nitrogen to freeze) at these locations. This destroys, or ablates, the tissue at these locations and interrupts the triggers for the heart arrhythmia. However, such catheter ablation procedures depend on the judgment of doctors and may not be precise or predictable, since there is no accurate way to determine the best location, time, and energy for ablation.

SUMMARY

Embodiments of the present invention provide a method and system for atrial fibrillation (AF) analysis, characterization, and mapping. Embodiments of the present invention provide a finite element model (FEM) based function model which can greatly improve the efficiency and precision for identifying AF disorders, predicting the occurrence of AF, mapping AF characteristics, and determining AF treatments, such as drug delivery and ablation usage.

In one embodiment of the present invention, an FEM representing a physical structure of a heart is generated. Electrogram data can be sensed at various locations in the heart using an electrophysiology catheter, and the electrogram data is mapped to the elements of the FEM. Function parameters, which measure some characteristics of AF arrhythmia, are then simultaneously calculated for all of the elements of the FEM based on the electrogram data mapped to the elements of the FEM. An artificial neural network (ANN) can be used to calculate the function parameters based on inputs including the electrogram data, patient data, and physical measurement data.

These and other advantages will be apparent to those of ordinary skill in the art by reference to the following detailed description and the accompanying drawings.

DETAILED DESCRIPTION

Embodiments of the present invention are directed to a method and system for atrial fibrillation (AF) monitoring and analysis, which provides an efficient and reliable approach for characterizing AF occurrence time, position, tissue volume, energy amount, as well as other AF characteristics. Embodiments of the present invention may be implemented in real-time in order to visualize a mapping of AF activity in a patient's heart. Embodiments of the present invention my also be capable of visualizing a mapping of various signal analysis calculations relating to the AF activity. Embodiments of the present invention can be used to indicate appropriate AF treatment based on various parameters.

Figure 1:
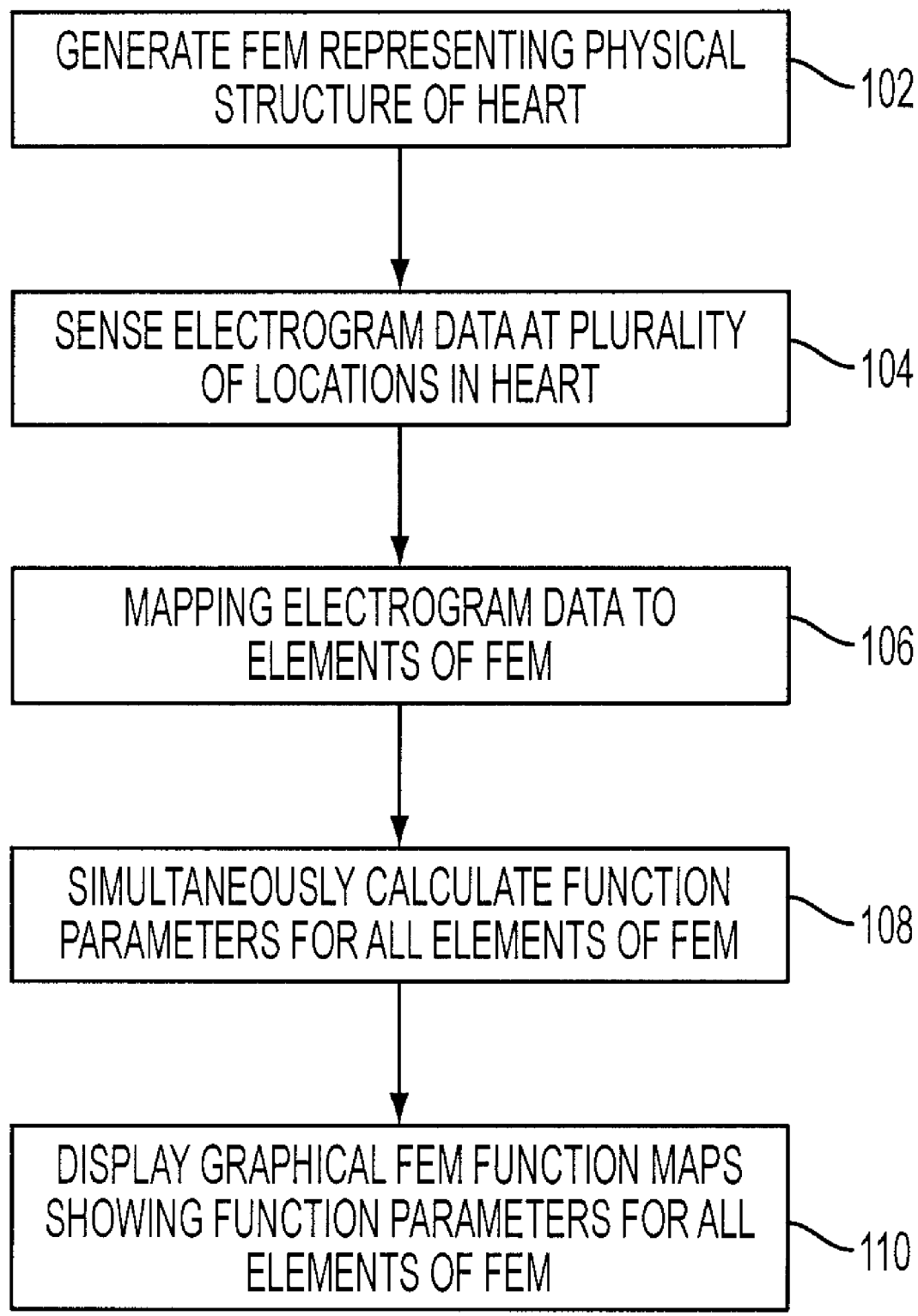
FIG. 1 illustrates an AF analysis and monitoring method according to an embodiment of the present invention.

FIG. 1 illustrates an AF analysis and monitoring method according to an embodiment of the present invention. This method may be performed by a processor of a computer system executing computer program instructions. The computer system may include a display configured to display images generated during the execution of the computer program instructions. As illustrated in FIG. 1, at step 102, a finite element model (FEM) representing the physical structure of a heart is generated. As is well known, an FEM is a mathematical model of the physical geometry of a structure. The FEM of the heart can be generated based on anatomical images of the heart. For example, the FEM can be generated based on MRI, CT, or angiography images of the heart. Such images can be converted into an FEM using known commercially available software. According to an embodiment of the present invention, the FEM of the heart can be a patient specific model generated using patient specific CT, MRI, or angiogram images. The generation of a cardiac FEM model is described in greater detail in Hashim et al., "Finite Element Method in Cardiac Surgery," *Interactive Cardiovascular and Thoracic Surgery* 5 (2006) 5-8, which is incorporated herein by reference. The FEM divides the physical structure of the heart into small finite segments known as elements. Accordingly, each element of the FEM represents a specific location in the physical structure of the heart. The FEM can be expressed mathematically as an FEM matrix made up of the elements, and can also be displayed in graphical form.

In order to generate an FEM of the heart, the heart can be segmented into finite elements based on the cardiac anatomical structure, via which a finite element matrix can be achieved to localize and diagnose the function of the each element. Specifically, each chamber of the heart can be mapped into finite element model with accurate dimension and position tracking information, both 2 D and 3 D. For example, based on pre-knowledge from an image, such as a CT image or an X-ray image, the maximum displacement and geometry of the heart can be derived. Then a 2 D structure can be built with the boundary condition and size information, which is utilized to create a finite element model by appropriately meshing a structure with 2 D elements. Usually a generic finite element model can be constructed and with some minute adjustments, such as size and boundary, of the constructed heart model, an accurate FEM can be created for cardiac function analysis and medical application.

At step 104, electrogram data is sensed a plurality of locations in the heart. As used herein, the electrogram data can be intra-cardiac electrograms which are intra-cardiac signals which show the electrophysiological activity at the locations in the heart. The Intra-cardiac electrograms can be sensed by an electrophysiology (EP) catheter, such as a Boston scientific basket lead system, or any other type of intra-cardiac lead system. The intra-cardiac electrograms show the electrical activity between two electrodes of the EP catheter. These signals are from the cardiac tissue closest to the electrode, displaying a localized area instead of the electrical activity of the whole heart, as in the case of a surface EKG. The plurality of locations can correspond to the elements of the FEM generated at step 102.

At step 106, the electrogram data is mapped to the elements of the FEM. The electrogram data sensed at each of the plurality of locations in the heart is mapped to a corresponding element of the FEM. Thus, each of the elements of the FEM has associated electrogram data which was sensed at the location in the heart corresponding to that element.

At step 108, function parameters are simultaneously calculated for all elements of the FEM. A Function parameter is defined herein as a measure of a characteristic of an AF arrhythmia or current condition of the heart based at least in part on the derived electrogram data mapped to the elements of the FEM. Various signal processing analyses are used to process the electrogram data mapped to each element of the FEM in order to generate various function parameters. By simultaneously calculating the function parameter of every element in the FEM, a comprehensive electrophysiological function image can be derived showing any of the calculated function parameters. For example, an FEM function map can be generated showing a function parameter such as excitation time mapping, dominant frequency mapping, AF energy level mapping with time, element to element intra-cardiac impedance, arrhythmia properties (which may be useful to decide the possibility of arrhythmia for every element and ablation sequence during multi-site arrhythmia cases), etc., for each element in the FEM. Using FEM function maps for the various function parameters, real-time electrophysiological function mapping can be implemented. Furthermore, there may be more calculated parameter mapping from the intra-cardiac electrograms corresponding to the FEM modeled function units, such as exciting variability mapping, frequency ratio mapping (compared with baseline), etc.

At step 110, graphical function maps showing function parameters for all elements of the FEM are displayed. For example, the function maps can be displayed on a display on a computer system performing the method by executing computer program instructions.

Figure 2:
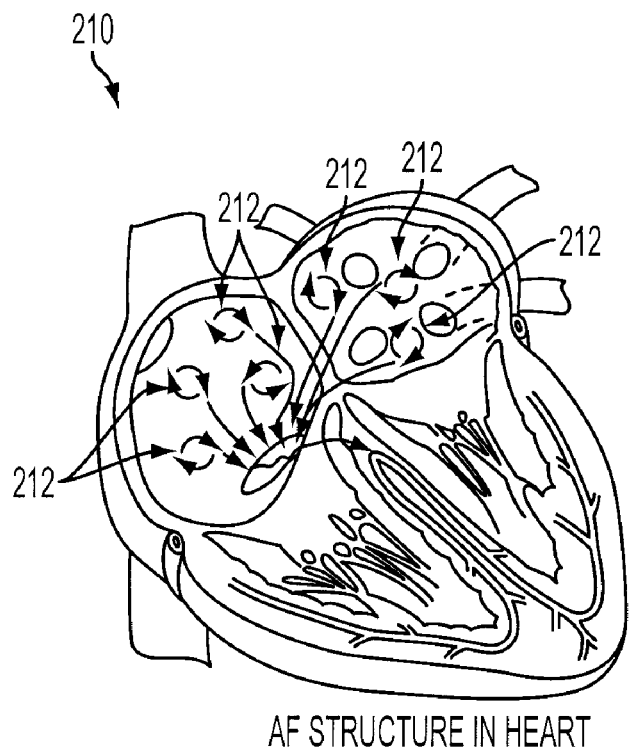
FIG. 2 illustrates an FEM based electrophysiological function map according to an embodiment of the present invention.
Figure 2:
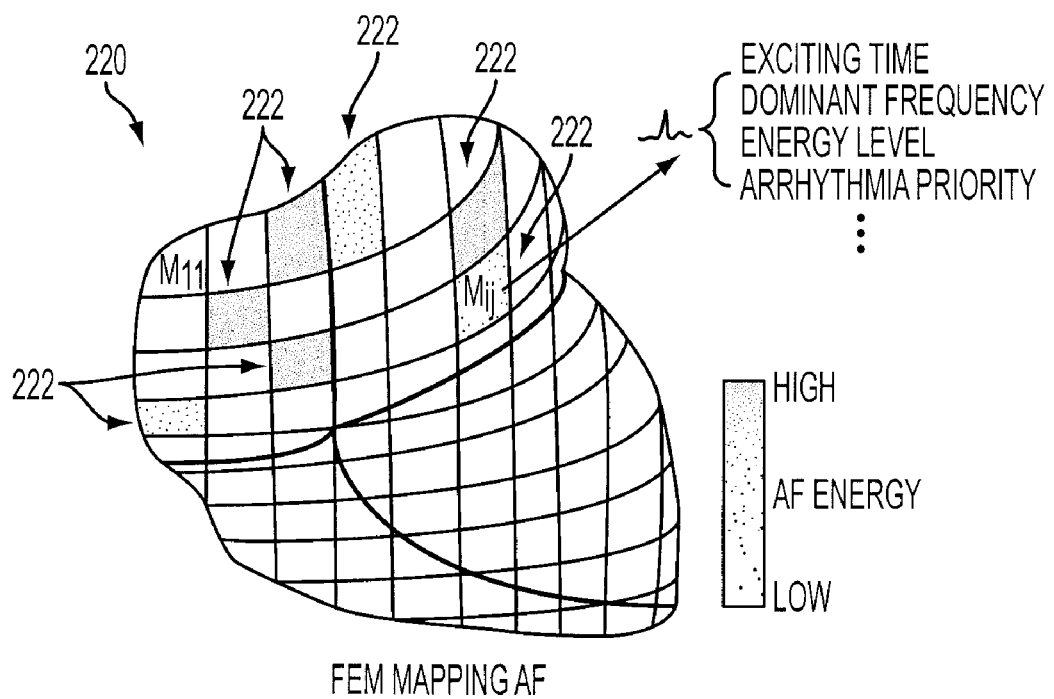

FIG. 2 illustrates an FEM based electrophysiological function map according to an embodiment of the present invention. As illustrated in FIG. 2, image 210 is an anatomical structure of a heart with multi-roller AF arrhythmias 212. The AF arrhythmias 212 are locations of abnormal electrophysiological activity in the heart. Image 220 is an FEM function map which shows the function parameter of AF energy level which is calculated based on electrogram data mapped to an FEM representing the anatomical structure of the heart. As shown in image 220, various elements 222 are shaded showing high levels of AF energy sensed in the electrograms for the corresponding location in the heart. These shaded elements 222 correspond to the AF arrhythmias 212 shown in image 210. The elements of the FEM function map 220 represent the smallest cardiac electrophysiological function units, whose size can be derived by the combination of the anatomical structure, the hardware precision of the lead which senses the electrogram data, and the function units of the cardiac tissue. For example, in FEM function map 220, element $M_{ij}$ is one of the function areas which is in AF arrhythmia rolling fibrillation. As shown in FIG. 2, a graphical representation of the FEM function map can be displayed to simultaneously show the function parameter of AF energy at each element of the FEM As illustrated in FIG. 2, an FEM function map 220 showing the AF energy for each element is displayed. Various other function parameters calculated based on the electrogram data for each element can be similarly displayed as a graphical FEM function map. For example, function parameters such as exciting time, dominant frequency, energy level, arrhythmia priority, etc., can be displayed as an FEM function map similar to the FEM function map 220 of FIG. 2. According to an embodiment of the present invention, the displayed function maps can be updated in real time, in response to real time changes in the electrogram data that is mapped to the elements of the FEM.

Various function parameters and FEM function maps may be used to determine function parameters, such as ablation priority and ablation locations, which determine treatment for an AF arrhythmia. The ablation priority function parameter is a priority assigned to each of the elements in the FEM, which determines which of the corresponding locations need ablation and in what order the ablation should be applied to the locations. The ablation locations function parameter determines for each element whether the corresponding location needs ablation. For example, ablation priority or ablation location can be determined, for each element, based on the AF energy of each element, which is illustrated in FIG. 2. It is also possible that ablation priority and ablation locations can be determined by another function parameter or some combination of function parameters.

Although the method of FIG. 1 is described as using a basket lead system to sense the electrogram data in the heart, the FEM modeling described above may also be utilized for catheters other than a basket lead system according to various embodiments of the present invention. For example, electrophysiological data for an element in the FEM may be derived from interpolation of neighboring elements if there are not enough leads to sense electrogram data for each element. Additionally, mapping the electrophysiological function and growing patterns along a single or individual catheter may be advantageous in some cardiac EP and coronary intervention applications. According to various embodiments of the present invention, the FEM mapping provides a model for EP study with adaptive image matching to anatomical structure by registration, such as angle and size changing, which may make it feasible to re-map the EP function parameters without complicated and time-consuming reinstallation and anatomical matching and registration procedure.

Although the method of FIG. 1 is described as mapping electrophysiological data, the FEM based function mapping described above is not limited to application in electrophysiology, and can be used to map anything. According to various embodiments of the present invention, the FEM modeling can also be used for intra-cardiac vital signs signals, such as tissue temperature mapping, pressure mapping, etc.

Figure 3:
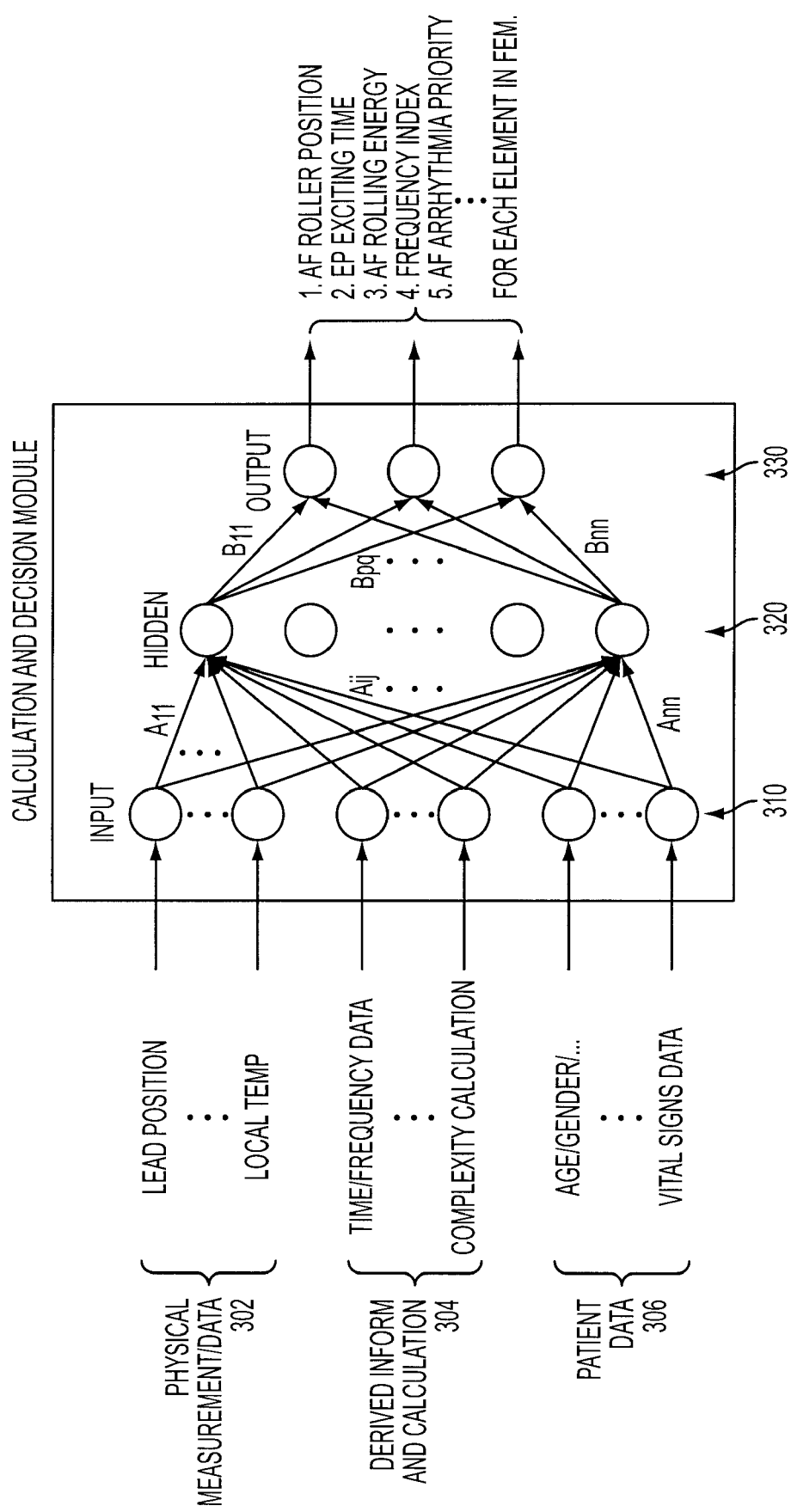
FIG. 3 illustrates a 3-layer ANN calculation and decision module for AF analysis according to an embodiment of the present invention.

According to an advantageous embodiment of the present invention, an artificial neural network (ANN) can be utilized to implement step 108 of FIG. 1 and calculate various function parameters for the elements of the FEM. The ANN can take into account various types of information, such as patient data, hem data, lead information, etc., in addition to the electrogram data mapped to each element in the FEM. A 3-layer ANN can be utilized in order to calculate the index and value, categorize the severity and healthy priority, and derive the function parameters for each element. FIG. 3 illustrates a 3-layer ANN calculation and decision module for AF analysis according to an embodiment of the present invention. As illustrated in FIG. 3, the ANN calculation and decision module includes an input layer 310, a hidden layer 320, and an output layer 330. Each of the layers 310, 320, and 330 include multiple modules which process data received at the modules. $A_{ij}$ and $B_{pq}$ are weights between the modules, which can be adaptively adjusted and tuned with training data. The ANN calculation and decision module has self-learning ability with new input data which can increase the accuracy of the calculated results for the FEM elements. The set-up and training of an ANN is described in greater detail in U.S. Pat. No. 5,479,572, which is incorporated herein by reference.

The ANN calculation and decision module can combine various types of information and data together. For example, the ANN calculation and decision module of FIG. 3 receives as input physical measurement data 302, such as lead position, local temperature, etc., derived information and calculations 304, which can be derived from the FEM mapping described above such as time/frequency data, complexity calculations, etc., and patient data 306, such as age, gender, vital signs, etc. These inputs are processed by the input layer 310, the hidden layer 320, and the output layer 330 in order to calculate function parameters which represent many characteristics of the AF arrhythmia, such as AF roller position, EP exciting time, AF rolling energy, Frequency index, AF arrhythmia priority, etc. Such function parameters are simultaneously calculated by the ANN calculation and decision module for each element in the FEM. Function parameters, such as ablation location and ablation priority, can be output from the ANN to suggest which locations in the heart need ablation and a priority for providing ablations for those locations. As described above, the function parameters of ablation location and ablation priority can be based on another function parameter, such as AF energy, or a combination of other function parameters.

With the comprehensive calculation and information fusion of the FEM elements based on ANN analysis, a 3-D cardiac electrophysiological function mapping image can be derived. This mapping method can be utilized for real time electrophysiological function mapping, which may be advantageous in localizing the cardiac arrhythmia position, pathology conducting sequence, abnormal tissue area, energy focus of the disorder and irregularity, etc. The real time electrophysiological function mapping can also be utilized for suggesting treatment of AF arrhythmias, such as a priority for ablation locations.

As described above, in an embodiment of the present invention, a 3-layer ANN module can be used for electrophysiological pattern analysis. However, an embodiment of the present invention is not limited to an ANN, and other analysis methods can be employed for the simultaneous calculation function parameters, such as Fuzzy model, expert system model, etc.

Figure 4:
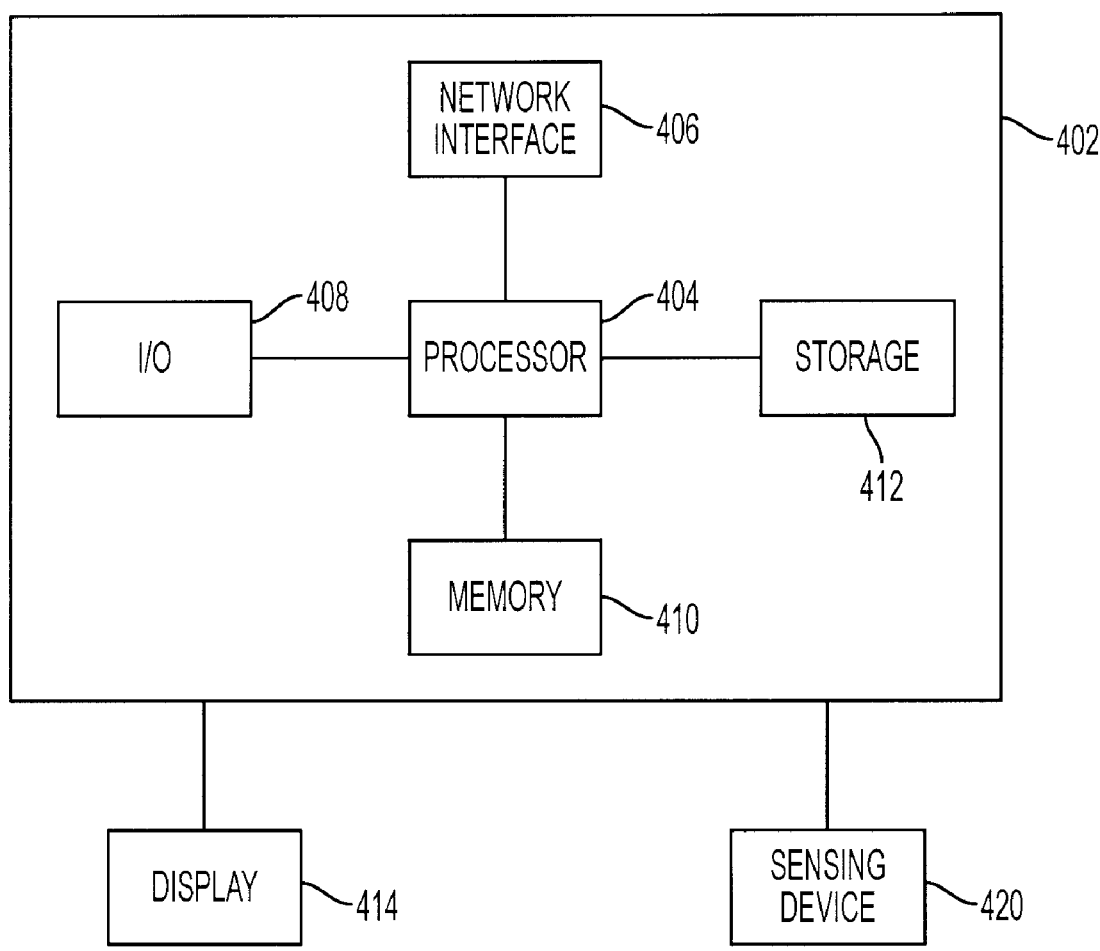
FIG. 4 is a high level block diagram of a computer capable of implementing an embodiment of the present invention.

The above-described method for AF analysis, characterization, and mapping can be implemented on a computer using well-known computer processors, memory units, storage devices, computer software, and other components. A high level block diagram of such a computer is illustrated in FIG. 4. Computer 402 contains a processor 404 which controls the overall operation of the computer 402 by executing computer program instructions which define such operation. The computer program instructions may be stored in a storage device 412 (e.g., magnetic disk) and loaded into memory 410 when execution of the computer program instructions is desired. Thus, applications for generating an FEM and mapping electrogram data to the elements of the FEM can be defined by the computer program instructions stored in the memory 410 and/or storage 412 and controlled by the processor 404 executing the computer program instructions. Furthermore, an ANN calculation and decision module can be defined as computer program instructions stored in the memory 410 and/or storage 412 and controller by the processor 404 executing the computer program instructions. A sensing device 420, such as an EP catheter, can be connected to the computer 402 to input electrogram data sensed in the heart to the computer 402. The computer 402 also includes one or more network interfaces 406 for communicating with other devices via a network. The computer 402 also includes a display 414 for displaying the graphical FEM function maps, which show the function parameters for each element of the FEM. The computer 403 also may include other input/output devices 408 that enable user interaction with the computer 402 (e.g., keyboard, mouse, speakers, buttons, etc.) One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
generating a finite element model (FEM) representing a physical structure of a heart,
said FEM comprising a plurality of elements each corresponding to a location in the heart;
sensing electrogram data at a plurality of location in the heart;
mapping said electrogram data for each of said plurality of locations to a corresponding one of said plurality of elements of said FEM;
concurrently calculating at least one functional parameter for each said plurality of elements of said FEM based on electrogram data mapped to the elements;
assigning an ablation priority based on the said functional parameter to individual element of said FEM enabling identification of a priority order of ablation and localization of tissue to be ablated in response to the sensed electrogram data.

2. The method of claim 1, further comprising:
using an artificial neural network in localizing cardiac arrhythmia positions in a heart indicating a priority order of ablation and location of tissue.

3. The method of claim 2, further comprising:
generating at least one FEM function map image showing said at least one function parameter for each of said plurality of elements and wherein
the step of assigning an ablation priority comprises assigning an ablation priority in response to detected Atrial Fibrillation energy of locations of said FEM.

4. The method of claim 3, further comprising:
displaying said FEM function map image; and
updating said FEM function map image in real time based on change in the electrogram data mapped to each of the plurality of elements of said FEM.

5. The method of claim 2, wherein said step of simultaneously calculating at least one function parameter for each of said plurality of elements of said FEM comprises:
applying at least one signal processing analysis to the electrogram data mapped to each of said plurality of elements of said FEM.

6. The method of claim 2, wherein said at least one function parameter comprises at least one of AF energy, excitation time, dominant frequency, energy level, and arrhythmia priority.

7. The method of claim 2, wherein the step of concurrently calculating at least one function parameter for each of said plurality of elements of said FEM comprises:
calculating said at least one function parameter for each of said plurality of elements of said FEM using an artificial neural network (ANN) which receives the electrogram data mapped to each of the plurality of elements of said FEM as input.

8. The method of claim 7, wherein said ANN receives patient data and physical measurement data as input, and said step of calculating said at least one function parameter for each of said plurality of elements of said FEM using an ANN comprises:
calculating said at least one function parameter for each of said plurality of elements of said FEM based on the electrogram data, the patient data, and the physical measurement data using said ANN.

9. The method of claim 2, wherein said at least one function parameter comprises an ablation location function parameter, which indicates, for each of said plurality of elements of said FEM, whether the corresponding location in the heart needs ablation.

10. The method of claim 2, wherein said at least one function parameter comprises and ablation priority function parameter, which determines, for each of said plurality of elements of said FEM, a priority for ablation.

11. The method of claim 1, further comprising:
displaying an FEM function map showing the electrogram data mapped to the plurality of elements of the FEM.

12. An apparatus comprising:
means for generating a finite element model (FEM) representing a physical structure of a heart, said FEM comprising a plurality of elements each corresponding to a location in the heart;
means for sensing electrogram data at a plurality of locations in the heart to correspond to one of said plurality of elements of said FEM;
means for concurrently calculating at least one functional parameter for each of said plurality of elements of said FEM based on electrogram data mapped to the element; and
means for assigning an ablation priority to individual elements of said FEM enabling identification of priority order of ablation and location of tissue to be ablated in response to sensed electrogram data.

13. The method of claim 12, further comprising:
using an artificial neural network in localizing cardiac arrhythmia positions in a heart indicating a priority order of ablation and location of tissue.

14. The apparatus of claim 13, further comprising:
means for displaying an FEM function map image showing said at least one function parameter for each of said plurality of elements;
means for updating said FEM function map image in real time based on change in the electrogram data mapped to each of the plurality of elements of said FEM; and wherein
the means for assigning an ablation priority assigns an ablation priority in response to detected Atrial Fibrillation energy of locations of said FEM.

15. The apparatus of claim 13, wherein said means for simultaneously calculating at least one function parameter for each of said plurality of elements of said FEM comprises:
means for applying at least one signal processing analysis to the electrogram data mapped to each of said plurality of elements of said FEM.

16. The apparatus of claim 13, wherein said means for simultaneously calculating at least one function parameter for each of said plurality of elements of said FEM comprises:
means for executing an artificial neural network (ANN) configured to calculate said at least one function parameter for each of said plurality of elements of said FEM based on the electrogram data mapped to the element.

17. The apparatus of claim 16, wherein said ANN receives the electrogram data, patient data, and physical measurement data as input, and said ANN is configured to calculate said at least one function parameter for each of said plurality of elements of said FEM based on the electrogram data, the patient data, and the physical measurement data.

18. The apparatus of claim 13, wherein said at least one function parameter comprises an ablation location function parameter, which indicates, for each of said plurality of elements of said FEM, whether the corresponding location in the heart needs ablation.

19. The apparatus of claim 13, wherein said at least one function parameter comprises and ablation priority function parameter, which determines, for each of said plurality of elements of said FEM, a priority for ablation.

20. The apparatus of claim 12, further comprising:
means for displaying an FEM function map showing the electrogram data mapped to the plurality of elements of the FEM.

21. The apparatus of claim 12, wherein said means for sensing electrogram data comprises and electrophysiology catheter.

22. A non-transitory computer readable medium encoded with computer executable instructions, the computer instructions defining steps comprising:
generating a finite element model (FEM) representing a physical structure of a heart, said FEM comprising a plurality of elements each corresponding to a location in the heart;
receiving electrogram data sensed at a plurality of locations in the heart;
mapping said electrogram data from each of said plurality of location to a corresponding one of said plurality of elements of said FEM;
assigning an ablation priority to individual elements of said FEM enabling identification of a priority order of ablation and location of tissue to be ablated in response to the sensed electrogram data, concurrently calculating at lease one functional parameter for each of said plurality of elements of said FEM based on electrogram data mapped to the elements; and identifying individual elements of said FEM for ablation and location of tissue to be ablated in response to determined Atrial Fibrillation energy locations of said FEM derived from the sensed electrogram data.

23. The computer readable medium of claim 22, further comprising computer executable instructions defining the steps of:

using an artificial neural network for localizing cardiac arrhythmia positions in a heart indicating a priority order of ablation and location of tissue.

24. The computer readable medium of claim 23, further comprising computer executable instructions defining the steps of:

displaying an FEM function map image showing said at least one function parameter for each of said plurality of elements;

updating said FEM function map image in real time based on change in the electrogram data mapped to each of the plurality of elements of said FEM; and assigning an ablation priority in response to detected Atrial Fibrillation energy of locations of said FEM.

25. The computer readable medium of claim 23, wherein the computer executable instructions defining the step of simultaneously calculating at least one function parameter for each of said plurality of elements of said FEM comprise computer executable instructions defining the steps of:

executing an artificial neural network (ANN) configured to calculate said at least one function parameter for each of said plurality of elements of said FEM based on the electrogram data mapped to the element.

26. The computer readable medium of claim 25, wherein said ANN receives the electrogram data, patient data, and physical measurement data as input, and said ANN is configured to calculate said at least one function parameter for each of said plurality of elements of said FEM based on the electrogram data, the patient data, and the physical measurement data.

27. The computer readable medium of claim 23, wherein said at least one function parameter comprises an ablation location function parameter, which indicates, for each of said plurality of elements of said FEM, whether the corresponding location in the heart needs ablation.

28. The computer readable medium of claim 23, wherein said at least one function parameter comprises and ablation priority function parameter, which determines, for each of said plurality of elements of said FEM, a priority for ablation.

29. The computer readable medium of claim 22, further comprising computer executable instructions defining the step of:

displaying an FEM function map showing the electrogram data mapped to the plurality of elements of the FEM.

\* \* \* \* \*